United States Patent
Medeiros Pinto et al.

(10) Patent No.: US 9,637,762 B2
(45) Date of Patent: May 2, 2017

(54) SYSTEM AND METHOD FOR THE INTEGRATED PRODUCTION OF FIRST AND SECOND GENERATION ETHANOL AND THE USE OF INTEGRATION POINTS FOR SUCH PRODUCTION

(71) Applicant: CTC-CENTRO DE TECNOLOGIA CANAVIEIRA S.A., Piracicaba (BR)

(72) Inventors: José Ricardo Medeiros Pinto, Piracicaba (BR); Oswaldo Godoy Neto, Piracicaba (BR); Juliana Conceição Teodoro, Piracicaba (BR); Danilo Ribeiro De Lima, Piracicaba (BR); Liliane Pires Andrade, Piracicaba (BR); José Augusto Travassos Rios Tomé, Piracicaba (BR); Célia Maria Araújo Galvão, Americana (BR)

(73) Assignee: CTC—CENTRO DE TECNOLOGIA CANAVIEIRA S.A., Piracicaba (BR)

( * ) Notice: Subject to any disclaimer, the term of this patent is extended or adjusted under 35 U.S.C. 154(b) by 0 days.

(21) Appl. No.: 14/389,090

(22) PCT Filed: Mar. 27, 2013

(86) PCT No.: PCT/BR2013/000094
§ 371 (c)(1),
(2) Date: Sep. 29, 2014

(87) PCT Pub. No.: WO2013/142934
PCT Pub. Date: Oct. 3, 2013

(65) Prior Publication Data
US 2015/0064762 A1     Mar. 5, 2015

(30) Foreign Application Priority Data

Mar. 30, 2012 (BR) .................... 10 2012 0072990 8
Dec. 20, 2012 (BR) ...................... 10 2012 032807 0

(51) Int. Cl.
*C12M 1/00*     (2006.01)
*C12P 7/10*     (2006.01)
(Continued)

(52) U.S. Cl.
CPC .................. *C12P 7/14* (2013.01); *C08H 8/00* (2013.01); *C10L 1/023* (2013.01); *C12M 21/12* (2013.01);
(Continued)

(58) Field of Classification Search
CPC .......... C12M 47/10; C12M 43/02; C12P 7/10; Y02E 50/16; Y02E 50/17
See application file for complete search history.

(56) References Cited

U.S. PATENT DOCUMENTS

2007/0117195 A1* 5/2007 Warner ...................... B09B 3/00
435/161
2008/0103748 A1* 5/2008 Axelrud ............... G05B 13/048
703/12
(Continued)

FOREIGN PATENT DOCUMENTS

BR         PI0503931 A      3/2007
BR         PI0703302 A2     3/2009
(Continued)

OTHER PUBLICATIONS

Dias, et al., "Production of bioethanol and other bio-based materials from sugarcane bagasse: Integration to conventional bioethanol production process", Chemical Engineering Research and Design. 87(9): 1206-1216. 2009.
(Continued)

*Primary Examiner* — Nathan Bowers
(74) *Attorney, Agent, or Firm* — Carter, DeLuca, Farrell & Schmidt, LLP (57) ABSTRACT

A system and a process for the production of ethanol and related products from lignocellulosic biomasses (second
(Continued)

generation—2G-ethanol), particularly from sugarcane bagasse and straw is provided, however not limited thereto, integrated with conventional processes for the production of ethanol (first generation—1G-ethanol) such as, for example, from sugarcane juice and/or molasses (either in sugar and ethanol plants or in autonomous distilleries), corn, grain, wheat, sugary sorghum, white beetroot, among others, including the recovery/reuse of streams and effluents. More specifically, an integrated process for the production of ethanol and related products where the process warrants increased efficiency particularly in the use of the raw material, steam, electric power and treated water is provided.

12 Claims, 6 Drawing Sheets (51) Int. Cl.
    C12P 7/14 (2006.01)
    C12P 7/06 (2006.01)
    C08H 8/00 (2010.01)
    C10L 1/02 (2006.01)
(52) U.S. Cl.
    CPC ............ *C12M 43/02* (2013.01); *C12M 45/09* (2013.01); *C12M 45/20* (2013.01); *C12P 7/06* (2013.01); *C12P 7/10* (2013.01); *Y02E 50/16* (2013.01); *Y02E 50/17* (2013.01); *Y02P 20/125* (2015.11); *Y02P 20/136* (2015.11)

(56) References Cited

U.S. PATENT DOCUMENTS

| | | | | |
|---|---|---|---|---|
| 2010/0055753 | A1* | 3/2010 | Geros | ............. C07C 29/88 435/165 |
| 2012/0006320 | A1* | 1/2012 | Nguyen | ............. D21C 1/00 127/34 |
| 2012/0022299 | A1 | 1/2012 | Vauk | |
| 2012/0041186 | A1 | 2/2012 | Pschorn et al. | |
| 2013/0175158 | A1* | 7/2013 | Kiuchi | ............. C12M 21/12 203/77 |
| 2013/0196424 | A1* | 8/2013 | Genta | ............. C12P 19/14 435/294.1 |

FOREIGN PATENT DOCUMENTS

| | | |
|---|---|---|
| BR | PI0708266 A2 | 5/2011 |
| BR | PI0904538 A2 | 7/2011 |
| BR | PI0802153 A2 | 10/2011 |
| BR | PI1101295 A2 | 7/2013 |
| WO | 2012/021950 A1 | 2/2012 |

OTHER PUBLICATIONS

Reynaldo Palacios Bereche, "Modelagem e integração energética do processo de produção de etanol a partir da biomassa de cana-de-açúcar", Tese de doutorado. Faculdade de Engenharia Mecanica. Universidade Estadual de Campinas. Campinas, SP. 2011.

Neto, "Integrarção das principais tecnologias de obtenção de etanol através do processamento de celulose (2ª geração) nas atuais usinas de processamento de cana-de-açúcar (1ª geraçaão)", Tese de mestrado. Escola Politécnica. Universidade de São Paulo, SP. 2009.

Dias et al., "Improving bioethanol production from sugarcane: evaluation of distillation, thermal integration and cogeneration systems", Energy. 36(6): 3691-3703. 2011.

Zaldivar et al. "Fuel ethanol production from lignocellulose: a challenge for metabolic engineering and process integration", Appl Microbial Biotechnol. 56(1-2): 17-34. 2001.

Cardona CA e Sanchez OJ, "Fuel ethanol production: process design trends and integration opportunities", Bioresource Technology. 98:2415-2457, 2007.

Rossell CEV et al., "Saccharification of sugarcane bagasse for ethanol production using the Organosolv process", International Sugar Journal. 107:192-195, 2005.

International Search Report issued in corresponding application No. PCT/BR2013/000094 on May 9, 2013.

* cited by examiner

SYSTEM AND METHOD FOR THE INTEGRATED PRODUCTION OF FIRST AND SECOND GENERATION ETHANOL AND THE USE OF INTEGRATION POINTS FOR SUCH PRODUCTION

CROSS REFERENCE TO RELATED PATENT APPLICATIONS

This application is a U.S. National Phase Application of International Patent Application No. PCT/BR2013/000094, filed on Mar. 27, 2013, which claims the benefit of and priority to Brazilian Patent Application No. 10 2012 0072990 8, filed on Mar. 30, 2012, the disclosures of each of which are hereby incorporated by reference herein in their entirety.

FIELD OF THE INVENTION

The present invention refers to a system and a method for integrated production of first and second generation ethanol, comprising the recovery of effluent streams and rendering energy efficient the joint production of first generation (1G) ethanol, obtained from sugarcane juice and/or molasses, corn, wheat, sweet sorghum, amylaceous (starchy) raw materials, white beetroot, among others, and of second generation (2G) ethanol, obtained from lignocellulosic biomasses such as sugarcane bagasse and straw, without being limited thereto, and/or from similar products. More specifically, the presently disclosed method constitutes an integrated process for the production of ethanol and similar products allowing an increased level of efficiency in terms of use of raw materials, steam, electric power and treated water.

BACKGROUND OF THE INVENTION

The great potential for use of biomasses for the production of ethanol is being demonstrated worldwide year after year, with the use of various technological configurations and based on the use of a substantially wide variety of biomass types, to wit: C4 plants—belonging to the genera *Lolium, Spartina, Panicum, Miscanthus*, and combinations thereof; sugarcane bagasse (originating from a grinding mill and/or diffuser), sugarcane straw (originating from the sugarcane harvesting process, either manual or mechanized); straw of cereals such as wheat, rice, rye, barley, oats, corn and similar materials (e.g., Napier grass—"switchgrass"); wood; stalks and stems of banana plants, cactaceae, paperboard, sawdust, newspapers; agro-industrial or municipal waste materials and combinations thereof.

In Brazil, the sugarcane business dates back to the colonization of the country (1532), this being the year when the first seedlings were introduced to the region. However, for more than 500 years to date, Brazil only uses one third of the energy that can be derived from the sugarcane—the juice—for manufacturing sugar and alcohol. Thus, it is possible to consider an increase in productivity and cost reduction in the bioenergy chain, not only by way of gradual progress of the technologies currently in use, but also through the advent of new technologies, such as the case of technologies for the production of second generation ethanol, that will allow large-scale utilization of the remaining two-thirds of the plant (the biomass comprised of bagasse and straw).

These materials—sugarcane bagasse and straw—represent the most appropriate biomasses for the production of ethanol from lignocellulosic sources in our country, not only due to comprising between 40% and 50% cellulose, but also due to the significant volume of those byproducts generated as derivatives in the production of sugar and 1G ethanol. In this scenario, the development of a process for the production of 2G ethanol that mainly takes into account the aspects of thermal and infrastructural integration with the production of 1G ethanol seems to constitute the most feasible option.

The instant application therefore refers to a system and a method that enable the installation of a plant (technology) for the production of second generation ethanol annexed to a conventional first generation ethanol plant (irrespective of the raw material that is processed), considering the integral use of the biomass, that is to say, of sugars obtained from the extraction of the juice and the carbohydrates present in the residue having been generated (fibers). This strategy allows the enhancement of the production capacity of sugar and alcohol production plants and also of autonomous distilleries spread worldwide, by way of the recovery of streams and/or effluents currently available in plants that are presently in operation, preserving the formerly existing energy self-sufficiency, by means of the concept of process integration. This concept is mainly intended to optimize the use of energy and to reduce the environmental impact caused by industrial processes. Thus, one object of the present invention consists in the provision of a process for joint (integrated) production of 1G/2G ethanol, comprising the recovery of streams and effluents generated in the 1G process, towards supplying a significant parcel of the energy required for operating the 2G plant.

The technology for the production of second generation (2G) ethanol in Brazil is still undergoing a maturing period, and at present it still does not have plants already installed and with relevant capacity for commercial scale production. This scenario implies an excellent opportunity for implementation of the objectives described in the instant application, due to the same being able to afford significant gains with relation to the recovery of energy and effluents.

The documents cited in the following constitute references to the prior art relative to schemes of energy utilization and reuse of process streams, however none of these schemes either anticipates or suggests the subject matter disclosed in the present invention.

The doctorate thesis with the title "*Modelagem e integração energetica do processo de produção de etanol a partir de biomassa de cana-de-açúcar*" [Modeling and energy integration of the process of production of ethanol from sugarcane biomass] (Bereche, R. P., presented at the School of Mechanical Engineering of the UNICAMP university [University of Campinas, State of São Paulo, Brazil] in Jul. 21, 2011) discloses a theoretical analysis of the existing individual operations in a sugarcane and alcohol (1G) processing plant (1G), in addition to possible technologies for the production of cellulose-derived ethanol (2G). In the thesis in question, the author cites the possibility of promoting energy integration between the 1G and 2G technologies, however restricting the scope of applicability thereof to the use of sugarcane bagasse for the production of 2G-ethanol and to the juice evaporation system as an alternative for energy integration of the processes mentioned above. The process for joint (integrated) production of 1G/2G ethanol as disclosed in the instant patent application differs from the mentioned doctorate thesis on disclosing as constituting sources of raw materials for the obtainment of 2G ethanol all residue derived from the harvest of sugarcane and/or other crops (lignocellulosic materials), in addition to presenting practical and feasible solutions for optimizing the consumption of process water and for the reuse of effluents within the industrial environment, entailing important environmental benefits. Thus, the thesis under consideration does not anticipate the state of the art that is disclosed in the present document.

The master's thesis with the title "*Integração das Principals Tecnologias de Obtenção de Etanol Através do Processamento da Celulose (2ª Geracao) nas atuais usinas de cana-de-açúcar (1ª Geração)*" [Integration of the Main Technologies for Obtainment of Ethanol By Means of Processing of Cellulose ($2^{nd}$ Generation) in current sugarcane processing plants ($1^{st}$ Generation)] (Bernardo Neto, O., presented at the Polytechnics School of the University of São Paulo in Mar. 25, 2009) discloses a bibliographic review regarding the various second generation technologies and proposes the process of gasification of surplus biomass as constituting the best alternative for enhancing the energy efficiency of a sugarcane processing plant. Thus, the mentioned dissertation differs from the instant application due to failing to anticipate or suggest the use of process streams and effluents to optimize the energy integration of the processes for production of 1G+2G ethanol.

The article bearing the title "*Production of bioethanol and other bio-based materials from sugarcane bagasse: Integration to conventional bioethanol production process*" (Dias et al., Chemical Engineering Research and Design, 2009, 87: 1206-1216) discloses a study on thermal integration in the distillery by way of the technique of double effect distillation, associated to the ORGANOSOLV technology for acid hydrolysis of sugarcane bagasse. This work differs from the instant application, and it neither anticipates nor suggests the present invention, particularly due to being solely restricted to thermal optimization within the distillery for the purpose of increasing the amount of surplus bagasse from the first generation process. Furthermore, the said article also fails to consider the reuse of effluents and the thermal integration between the first and second generation processes for the production of ethanol, as claimed in the instant application.

The article with the title "*Improving bioethanol production from sugarcane: evaluation of distillation, thermal integration and cogeneration systems*" (Dias et al., Energy, 2011, 36(6): 3691-3703) discloses a study of energy optimization of a sugarcane plant ($1^{st}$ generation) by means of use of specific thermal integration for the distillation process, combined with the use of electric power cogeneration using the BIGCC—"Biomass Integrated Gasification Combined Cycle"—technology. This document neither anticipates nor suggests the system and method for energy integration of the technologies for the production of first and second generation ethanol as proposed herein, since it does not take into consideration the process for the production of cellulosic ethanol as constituting an alternative for the use of the biomass and it does not contemplate any solutions for reuse of effluents.

In patent application No. [BR] PI 0708266-5 A2 there are described a system and a method for the production of alcohol by distillation with energy optimization using the multiple effect technology. In this process, the feed to the distillation columns is split into two streams and fed to two sets of columns, one of these being a high pressure column and the other being a low pressure column, together with a reboiler which uses the thermal energy derived from the top of one column to supply heat to the other. This process demonstrates that when the system is adequately configured, it is possible to recover the heat available at the top of rectifying column B, however it does not indicate any applications external to the distillery. The present invention differs from this cited application on disclosing the use of streams available in the distillery, for example, in an associated second-generation ethanol production plant, applying the concept of integration of processes.

In patent application No. [BR] PI 0503931-2 A there is described an arrangement and a method for the production of anhydrous alcohol by way of a process of "Pressure Swing Adsorption" with energy optimization. In this process, a part of the heat contained in the end product (Anhydrous Alcohol) is recovered by means of thermal integration and mechanical compression of the anhydrous alcohol vapor, evidencing that when the process is configured in a well-structured manner, the recovery of the heat available in a stream with alcohol vapors is feasible. Application No. [BR] PI 0503931-2 A differs from the present invention in the fact that it discusses the application of the heat recovery technique in a specific manner for optimizing the consumption of vapor in the hydrated alcohol dehydration technology itself, however failing to discuss the thermal integration with any other process, and particularly with the technology for production of second generation ethanol.

In patent application No. US 2012/0041186 A1 there are described a method and a system for continuous pre-extraction of hemicellulose by vapor explosion treatment. In the said document, the "flash" stream has great energy potential for use in thermal recovery systems, although the cited document makes no mention to such applications. The present invention differs from the mentioned document due to using available and adequate streams from associated technologies/plants or in different sectors of the same process, in an integrated process concept.

In international publication No. WO 2012/021950 there is described a method for obtainment of an end stream of hydrolyzed product with high sugar content. The hydrolysis reaction system achieves its best efficiency level when the reaction temperature remains around 50° C. This characteristic of the hydrolysis system entails the need of a heat source in order to maintain the system at the specified temperature. However, the cited document does not suggest any specific strategy, arrangement, system and configuration for obtainment of the necessary energy to heat and maintain the optimum temperature in the hydrolysis system. The present invention differs from the said document in that it utilizes the streams/effluents generated in the conventional ethanol production process (irrespective of the raw material used in such process) to supply the energy required to heat the hydrolysis reactors and/or other equipment units of the 2G-ethanol plant.

In patent application No. [BR] PI 1101295-1, which applicant is Centro de Tecnologia Canavieira (CTC), there is described the use of vinasse (stillage) (raw, filtered, concentrated, etc.) and/or of any residue derived from the process of distillation of fermented wine as an alternative buffering agent in the process of enzymatic hydrolysis of lignocellulosic biomasses. The reuse of this and other effluents available in the conventional 1G-ethanol plants in combination with the present invention enhances the benefits that can be derived from the integrated process described in the present specification.

In patent application No. [BR] PI 0904538-4, filed by Centro de Tecnologia Canavieira (CTC), there is disclosed a process for optimizing the treatment of the plant biomass for the production of carbohydrates, ethanol and similar products, with the adoption of a process configuration which minimizes the total energy requirements of the industrial unit, on comparison with techniques currently employed and already well known. The said document evidences a complementary characteristic with relation to the present invention although it does not anticipate the objects that are claimed herein.

Based on what is gathered from the literature having been researched, there are not known to exist any documents that might anticipate or suggest the teachings of the present invention, so therefore the solution proposed herein is novel and evidences inventive step over the prior art.

SUMMARY OF THE INVENTION

In one aspect, the invention provides a system for integrated production of ethanol of first and second generations, comprising the following points of integration:

i) Use of the stream of flegmass (3) originating from the rectifying column(s) (B and/or B1) as a source of hot water for generating steam in the vessel (RF);

ii) Use of the stream of flegmass (3) originating from the rectifying column(s) (B and/or B1) as a source of hot water for the separation and recovery system in (S1) and (S2);

iii) Use of the stream of flegmass (3) originating from the rectifying column(s) (B and/or B1) as a source of hot water for controlling the solids content in the enzymatic hydrolysis step;

iv) Use of the stream of flegmass (3) originating from the rectifying column(s) (B and/or B1) as a source of hot water for directly or indirectly heating the enzymatic hydrolysis reactor(s) (RH);

v) Use of the stream of flegmass (3) originating from the rectifying column(s) (B and/or B1) as a source of hot water for cleaning the biomass on entry thereof into the process;

vi) Use of the alcoholic stream (4) from the top of the rectifying column(s) (B and/or B1) in vapor phase, as a source of heating for the biomass hydrolysis reactor(s);

vii) Use of the stream of vinasse (stillage) (5) as a source of direct or indirect heating for the biomass hydrolysis reactor(s) (RH);

viii) Use of the stream of vinasse (stillage) (5) as a source of buffering solution for controlling the pH level in the enzymatic hydrolysis reaction;

ix) Use of the energy contained in the "flash" vapor stream (6), generated after the pretreatment of the biomass, in order to generate steam in the vessel (RF);

x) Use of the vapor generated in the steam vessel (RF), stream (7), to provide energy for operating the stripping column(s) A and degassing column(s) A1 and of the rectifying column(s) (B and/or B1) or equivalent(s) thereof;

xi) Use of the vapor generated in the steam vessel (RF), stream (11), derived from stream (7), as a source of direct or indirect heating of the biomass hydrolysis reactor(s);

xii) Use of the vapor generated in the steam vessel (RF), stream (7), as a source of direct heating, that is, spurting (stream 8), at the bottom of columns A, A1, B and B1;

xiii) Use of the return flow of all or part of the condensate of the vapor of stream (7), when the energy is recovered by indirect exchange, for the steam vessel RF;

xiv) Use of treated water, stream (9), for generating steam in the RF vessel; and xv) Use of the steam generated in the vessel (RF), stream (10), to provide energy for preheating the feed stream(s) of the reactor (RPT) or equivalent(s) thereof;

and combinations thereof.

In one form of realization, the system further comprises the following elements:

i) at least one means for connecting the outlet of the vessel (TF) to the inlet of the steam vessel (RF);

ii) at least one means for connecting the outlet(s) of the rectifying column(s) (B and/or B1) to the steam vessel (RF);

iii) at least one means for connecting the outlet(s) of the rectifying column(s) (B and/or B1) to the separation and recovery systems in (S1) and (S2);

iv) at least one means for connecting the outlet(s) of the rectifying column(s) (B and/or B1) to the hydrolysis reactors (RH) and/or to the biomass cleaning system (TL);

v) at least one means for utilizing treated water available in the plant to generate steam in the vessel (RF);

vi) at least one means for connecting the outlet(s) of the steam vessel (RF) to the stripping column(s) A and degassing column(s) A1 and to the rectifying column(s) (B and/or B1) or equivalent(s) thereof;

vii) at least one means for connecting the outlet(s) of the steam vessel (RF) to the reactor(s) (RPT) or equivalent(s) thereof;

viii) at least one means for connecting the outlet(s) of the steam vessel (RF) to the hydrolysis reactor(s);

ix) at least one means for returning the condensate of the vapor of stream (7), when the energy is recovered by indirect exchange, to the steam vessel RF; and x) at least one means for employing the alcoholic stream (4) from the rectifying column(s) (B and/or B1) in vapor phase as a heat source for heating the biomass hydrolysis reactor(s), and combinations thereof.

In one form of realization, the said means are heat exchangers of the shell and tube type and/or plates, and the said system uses instrumentation and control in the vessel RF, that may further consist in pressure control means, level control means, flow control means, and temperature control means.

In one other aspect, the invention provides a process for the integrated production of ethanol of first and second generations, comprising the steps of:

i) Pretreatment of the biomass;

ii) Enzymatic hydrolysis of the pretreated biomass;

iii) Separation of the solution containing the fermentescible sugars from the residual lignin-rich fiber (cellulignin);

iv) Fermentation of the solution obtained in step iii) together with the sugars of the sugarcane juice and/or molasses;

v) Separation of the fermented wine; and vi) Distillation/dehydration of the ethanol produced in step v).

In one form of realization, in the said process:

i) the pretreatment of the biomass is performed by using steam, whereby a part of the energy employed in this operation is reused by means of the heat recovery system;

ii) the separation of the sugars generated in the pretreatment is conducted by using a part of the flegmass stream (3), originating from the rectifying column(s) (B and/or B1) and/or cleaning of the fermenters;

iii) the enzymatic hydrolysis of the pretreated biomass is conducted using as a heating source the flegmass stream (3); hydrated alcohol vapor stream (4) originating from the alcohol-rectifying column and/or from the vinasse (stillage) stream (5);

iv) the separation of the solution containing the desired sugars from the residual lignin-rich fiber (cellulignin) is conducted using a part of the flegmass stream (3), originating from the rectifying column(s) (B and/or B1) and/or cleaning of the fermenters;

v) the fermentation is conducted using a part of the streams stored in the heat recovery system (vapor stream generated in the vessel (RF), stream (7), and/or the flegmass stream (3)) for cleaning, sterilization, cooling or a combination of these operations;

vi) the separation of the fermented wine is conducted using a part of the stream stored in the heat recovery system, vapor stream generated in the vessel (RF), stream (7), and/or the flegmass stream (3), for cleaning, sterilization, cooling or a combination of these operations;

vii) the distillation/dehydration of the ethanol is conducted using a part of the stream stored in the heat recovery system, preferably the vapor stream generated in the vessel (RF), stream (7).

In one other form of realization, the process optionally comprises a step of cleaning of the biomass before the pretreatment step i), which may be conducted by using a part of the flegmass stream (3) originating from the rectifying column(s) (B and/or B1) and/or cleaning of the fermenters.

In one other form of realization, in step v), the molasses is diluted with the hydrolyzed juice until that a concentration between 10° Brix and 50° Brix is reached.

In one form of realization, the said heat recovery system is comprised by heat exchangers, separation vessels, control systems and further accessories required for the continuous and stable operation thereof.

In yet another form of realization, the process, in the said step i), may additionally be conducted with the use of chemical or biological catalysts.

In one other aspect, the invention refers to the use of the integration points as defined above for the integrated production of ethanol of first and second generations.

DETAILED DESCRIPTION OF THE INVENTION

All technical terms and expressions have the same meaning as commonly understood by a technician skilled in the art to which the present invention pertains. Although methods and materials similar or equivalent to those described herein may be used in the realization or testing of the present invention, the methods and materials that are deemed adequate in such connection are described below herein. Thus, the nomenclature cited herein might change in different units, industries or countries, however the technical concept and the scope of the present invention shall nonetheless remain valid. Furthermore, the materials, methods and examples presented herein are meant to be illustrative and not limitative in relation to the present invention.

The combination of the first and second-generation processes for the production of ethanol, for example, from sugarcane, allows the obtainment of a larger final amount of this biofuel without entailing thereby any increase in volume of cultivated raw material or any increase of planted area. The present invention provides a form of reuse of effluents and integration of energy of the technologies of first (1G) and second (2G) generations for the production of ethanol, biofuels in general and/or various chemicals (solvents, acids, polymers, among others) from lignocellulosic biomasses, particular the bagasse and the straw from sugarcane plants, however without being limited thereto.

For the purposes of the instant application, integration points relate to points where the 1G and 2G processes may be interlinked, by means of recovery and utilization of energy and/or effluent streams between the 1G and 2G ethanol production plants.

The First and Second-Generation Ethanol Production Plants

Figure 1:
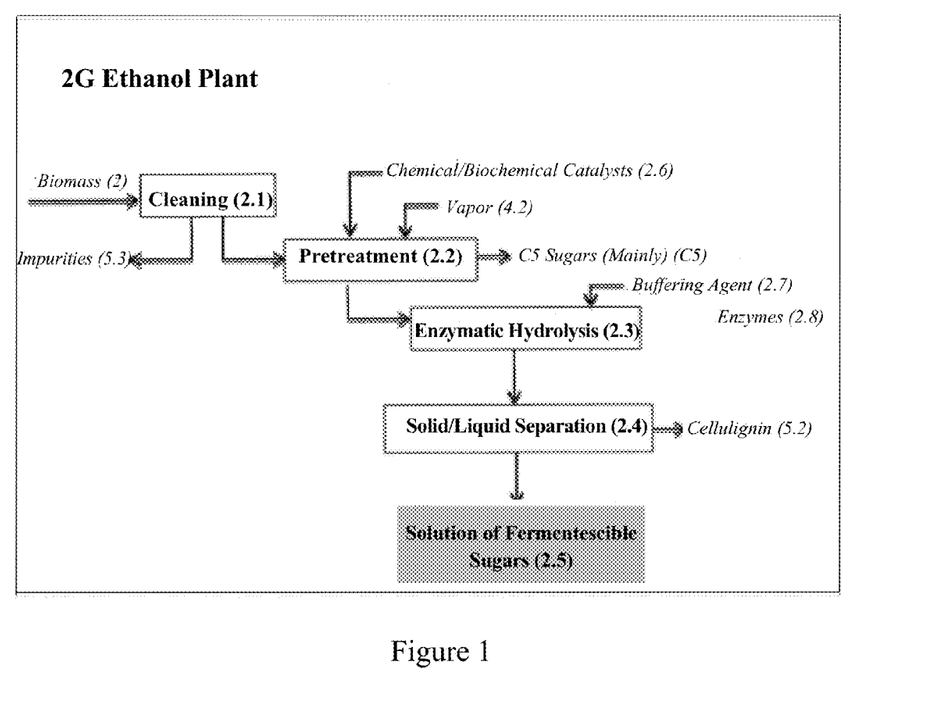
In FIG. 1 there is shown a schematic drawing of the process for utilization of lignocellulosic biomasses and the conversion thereof to fermentescible sugars, wherein the steps comprise cleaning (2.1), pretreatment (2.2), enzymatic hydrolysis (2.3) and solid-liquid separation (2.4) for the generation of a solution of fermentescible sugars (2.5). There are also shown the inlets and outlets such as for biomass (2), impurities (5.3), chemical/biological catalysts (2.6), steam (4.2), sugars (the majority thereof being of the type having five carbon atoms) (C5), buffering agent (2.7), enzymes (2.8) and cellulignin (5.2).

The second-generation (2G) ethanol production plant to be integrated to the first generation (1G) plant is basically represented by the steps illustrated in FIG. 1.

For the purposes of the present application, the term "biomass" may include any non-fossilized organic material, that is, one that is not derived from biological organisms, either alive or dead. As used herein, the term "biomass" refers particularly to the cellulosic or lignocellulosic biomass derived from plants, and includes material comprising cellulose and optionally further comprising hemicellulose, lignin, starch, oligosaccharides and/or monosaccharides. The biomass may be derived from one sole source or may comprise a mixture derived from more than one source. For example, a biomass may comprise a mixture of material of different plant species and/or different parts of plants. Biomass includes, without being limited to bioenergy crops, agricultural and forestry residues. Examples of biomass include, but are not limited to plant material derived from a plant selected from among the group consisting of sugarcane, corn, soybean, sorghum, millet rye, wheat, triticale, oat, barley, rice, alfalfa, Napier grass, *Miscanthus*, cotton, agave, hemp, jute, *eucalyptus*, pine, willow, tobacco, clover, bamboo, linen, sweet potato, potato, manioc, yarn, beetroot and canola. In a preferred embodiment, the biomass is comprised by sugarcane bagasse and/or sugarcane straw.

Initially the biomass arriving at the process may be subjected to a cleaning or conditioning step for removal of plant or mineral impurities that might be present in the material. This operation, albeit optional, is most relevant since it directly influences the final quality of the raw material that will be actually processed, and particularly since it extends the useful life of the installed equipment, as it substantially minimizes the damage related to abrasion due to the presence of, for example, sand and stones, particularly upon the material having been mechanically harvested. Thus, the cleaning of the biomass constitutes the first step of the process of production of 2G ethanol and it may be conducted using various different techniques (single operations), to wit: filtration, decanting, flotation, sedimentation, grinding, washing followed by filtration, sieving and dry cleaning, among others, without however being limited thereto.

In the second step of the process, the biomass (either or not cleaned and conditioned) is subjected to a pretreatment aimed at separating the three main (macro) fractions of the biomass and solubilizing non-cellulosic components, predominantly hemicelluloses, to facilitate accessibility to cellulolytic enzymes that are in charge of breaking down the cellulose molecule into (monomeric) glucose at the subsequent hydrolysis step. This separation/solubilization process occurs due to the action of chemical agents (e.g., acids and alkalis) and/or biological agents (e.g., enzymes, microorganisms), and generally under operating conditions of temperature and pressure that range from 150° C. to 225° C. and from 12 bar to 25 bar, respectively.

Among the many forms of conducting an efficient pretreatment, the following have emerged as constituting the most promising options: steam explosion (explosion with steam), hot water (hydrothermolysis), wet alkaline oxidation, wet alkaline peroxide oxidation, ammonia fiber oxidation (AFEX), sodium hydroxide fiber oxidation (SHFEX), $CO_2$ explosion and supercritical $CO_2$. In general, such methods use water vapor, diluted sulfuric acid, diluted phosphoric acid, ammonia, calcium hydroxide ("lime") and sulfur dioxide ($SO_2$).

Upon the conclusion of the pretreatment step (irrespective of the technique selected for such purpose), the pretreated material may progress through the process along what basically amount to two routes: 1) it may be directly fed to the hydrolysis step or 2) it may be subjected to an operation of solid-liquid separation whereby the pentoses liquor generated due to the solubilization of the hemicelluloses is separated (by means, for example, of compression, centrifugation, washing followed by filtration, washing followed by decanting, washing followed by evaporation, among others, however not limited thereto) and the remaining fibers (cellulose+lignin) are set to the subsequent hydrolysis step. This is one of the most relevant operational steps in terms of direct cost, in addition to substantially influencing the costs of the previous and subsequent steps of the process.

In the enzymatic hydrolysis step the cellulose remaining in the fiber after the pretreatment, irrespective of the method used for that purpose, is converted to glucose by the action of a "pool" of enzymes designated as cellulases. This hydrolytic process occurs generally in a buffered medium.

The enzymatic hydrolysis process may take place in any configuration selected from among the group that comprises SHF (Separate Enzymatic Hydrolysis and Fermentation), SSF (Simultaneous Enzymatic Hydrolysis and Fermentation), SSCF (Simultaneous Enzymatic Hydrolysis, Fermentation and Co-Fermentation), CBP (Simultaneous Enzyme Production, Enzymatic Hydrolysis and Fermentation), SEPHY (Production of Enzymes and Enzymatic Hydrolysis Separately from Fermentation) and combinations of the same.

Upon conclusion of the hydrolysis step, the hydrolyzed liquor containing the fermentescible sugars (C6) is separated from the residual solid fraction. This fraction is herein designated as cellulignin and is basically comprised of concentrated lignin and cellulose not converted in the hydrolytic process. In general, in this step of the process there may be used solid-liquid separation techniques such as filtration (with or without the use of vacuum), centrifugation, evaporation and decantation, among others. After the separation, the hydrolyzed liquor may proceed to fermentation or may be used as raw material for the production of a varied assortment of products such as fuels, organic acids, solvents and/or HMF (5-hydroxymethylfurfural), a compound generally used in the manufacture of softeners, lubricants, chemical products and polymers, among others. In this possible, it is possible to operate with or without cell recycling and in continuous mode, semi-continuous mode (fed-batch) or discontinuous mode (batch).

Figure 3:
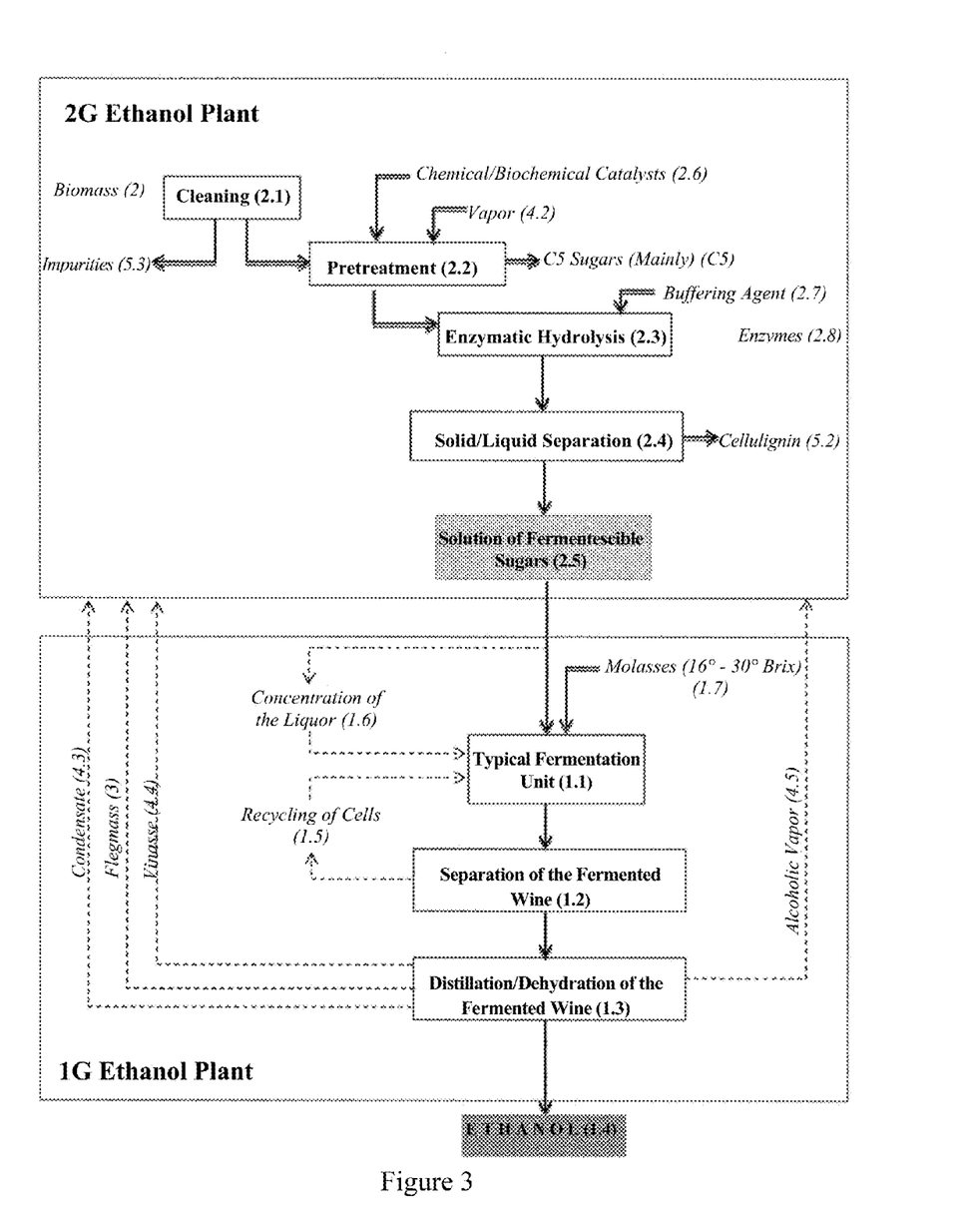
FIG. 3 shows a schematic drawing of the integrated process for the production of ethanol of first (1G) and second (2G) generations, comprising the reuse of streams and effluents having been generated for supplying the energy requirements of the global process, indicating the steps of the integrated process such as cleaning (2.1), pretreatment (2.2), enzymatic hydrolysis (2.3), solid-liquid separation (2.4), fermentation (1.1), separation of the fermented wine (1.2), distillation/dehydration of the fermented wine (1.3), in addition to its byproducts such as a solution of fermentescible sugars (2.5) and ethanol (1.4). There are further shown the inlets and outlets such as for biomass (2), impurities (5.3), chemical/biological catalysts (2.6), steam (4.2), sugars mostly with five carbon atoms (C5), buffering agent (2.7), enzymes (2.8), cellulignin (5.2), condensate (4.3), flegmass (3), vinasse (stillage) (4.4), cell recycling (1.5), concentration of the hydrolyzed juice (1.6), molasses (16°-30° Brix) (1.7) and alcoholic vapor (4.5).

The industrial base currently installed in the Brazilian plants uses the sugarcane for the production of sugar and ethanol, by means of processes that already share some operations such as, for example, the washing of the cane (with water or dry-cleaning), the preparation of the cane for grinding or diffusion, the extraction of the juice (which may be performed by grinding or diffusion) and the purification/treatment of the liquor thus obtained. In a similar manner, it would also be possible to recover lignocellulosic residues, particularly cane bagasse and straw, in order to increase the production of ethanol, biofuels in general and/or chemicals, by processing these biomasses in full integration with the existing facilities, particularly with regard to the energy issue. In FIG. 3 there is depicted a schematic drawing of the process for integrated production of ethanol of first and second generations, which is aimed at perfect integration between the various operations of both processes, energy recovery and reuse of effluents.

Within this context, the present invention relates to a system and a method for integrated production of ethanol (1G+2G) and similar products, comprising the integration of energy and of effluents between the two processes and providing an increased efficiency in the use of the raw material, steam, electric power, and treated water.

Integrated Process for the Production of Ethanol of First and Second Generations The present invention provides a process for integrated production of ethanol of first and second generations, which comprises, in broad terms, the following steps:

i) Pretreatment of the biomass;
ii) Enzymatic hydrolysis of the pretreated biomass;
iii) Separation of the solution containing the fermentescible sugars from the residual lignin-rich fiber (cellulignin);
iv) Fermentation of the solution having been obtained in step iii) together with the sugars of the sugarcane juice and/or molasses;
v) Separation of the fermented wine;
vi) Distillation/dehydration of the ethanol produced in step v).

Figure 6:
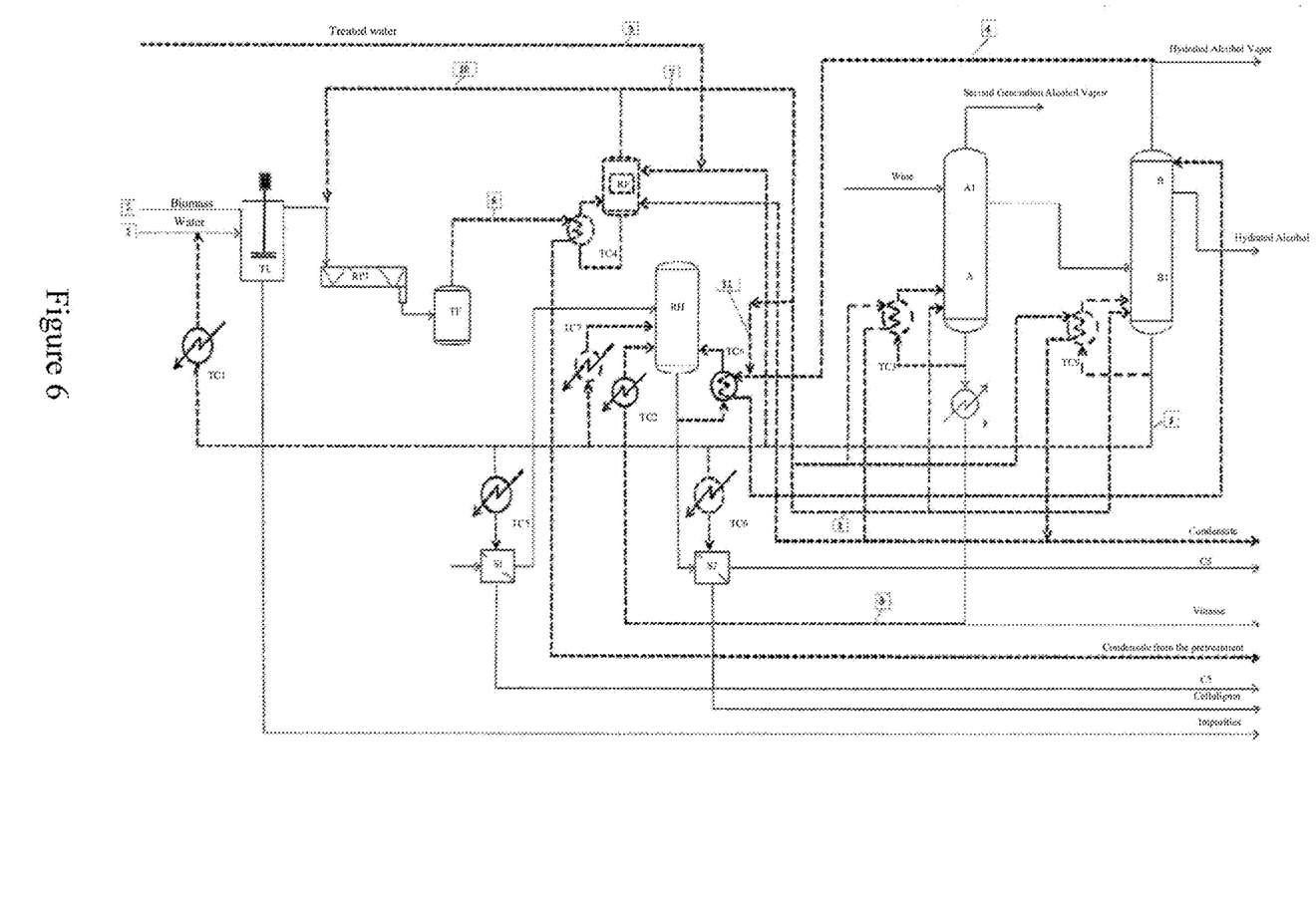
FIG. 6 shows the system for integrated production of first and second generations ethanol according to the instant application, comprising the reuse of energy and effluents in accordance with the present invention. The Figure shows the essential, preferred and optional streams and equipment, pointing out the integration points for reuse of energy and effluents between the second generation ethanol production plants and the hydrated alcohol production plant.

Optionally, prior to the above described step i), the biomass may be cleaned. In one embodiment, the first step of the process according to the present invention consists in cleaning the raw material using the "TL" cleaning system, aimed at removing impurities and homogenizing the biomass, to render the same more accessible to subsequent chemical and/or biological treatments, as well as to protect the equipment from possible mechanical wear caused by the presence of mineral impurities. This system may exhibit various configurations, may be comprised by various equipment units and may make use of various concepts for separating the impurities and render the raw material adequate to the conditions of the subsequent processes, as is known by a technician skilled in the art. Within the universe of possible cleaning systems, there exist technological solutions that employ a tank or equivalent vessel with clean water and stirring means for removing impurities and homogenizing the biomass, as depicted in FIG. 6. In a form of realization of the present invention, the cleaning is performed with water such as, for example, from the flegmass stream (3) (see FIG. 6).

The following step consists in the chemical and physical alteration of the biomass, also named pretreatment, with solubilization of the hemicellulosic fraction. In this step, high-pressure steam or low-pressure steam is fed to the pretreatment reactor (a procedure commonly designated as steam explosion), containing biomass that may either be or not be impregnated with catalysts. Optionally there may be used chemical catalysts (e.g., acids and alkalis) and/or biological catalysts (e.g., enzymes, microorganisms).

Within the scope of the present invention, typical distillery streams and/or effluents may be used in this step of the process, contributing to the energy optimization of the integrated 1G/2G process and entailing obvious environmental benefits. For example, the biomass may be treated with vapor originating from steam stored in a heat recovery system "RF". After the desired time of residence, the treated biomass is sent to a "flash" tank "TF". The vapor generated in this step, free of the particles of biomass, is used totally or partially as a heat source for heating the internal streams of the process of production of ethanol of second generation, as disclosed in the instant application. Subsequently, the pretreated biomass is sent to a separation system "S1" (separation by filtration, centrifugation, extraction by diffusion, etc.) for recovery of the C5 sugars originated from the hemicellulose, having been solubilized during the pretreatment. In one form of realization, the separation may take place with the use of a part of the flegmass stream (3), as a source of hot water (see FIG. 6).

Continuing the process sequence, the pretreated biomass is sent to the enzymatic hydrolysis system "RH", wherein the cellulose is mostly converted to glucose by way of different approaches that may include complex and/or multiphase technologies. The hydrolytic process generally occurs in a buffered medium and at controlled temperatures.

Within the scope of the present invention, one alternative form of realization, as regards the buffering of the medium, consists in the use of vinasse (stillage) or of any other residue from the distillation of fermented wine (irrespective of its origin or form of presentation—raw, filtered, concentrated, etc.) in the process of saccharification of lignocellulosic biomasses, which evidences various advantages on comparison with the conventional processes. Such reuse represents a possible point of integration between the 1G and 2G processes. Some competitive advantages related to the use of the vinasse (stillage) in the process as proposed herein are the following: 1) significant economy in the consumption of water in the step of enzymatic hydrolysis of biomasses (either or not pretreated), since the vinasse (stillage) may further substitute all the water required in this specific step; 2) significant reduction in costs (more affordable cost) relatively to the acquisition of chemical inputs for buffering the medium (pH control); 3) high efficiency in the buffering of the reaction medium wherein occurs the saccharification of lignocellulosic biomasses; 4) availability in the industrial environment itself, in large amounts, since that for every liter of ethanol that is produced there are generated about 10 to 12 liters of vinasse (stillage); 5) richness in nitrogen (up to 1 g/L of total nitrogen in its composition), which is a macronutrient of extreme relevance to the fermentation process; and 6) fulfillment of environmental requisites, since it allows a "residue" with high biochemical oxygen demand (BOD) to be reused in the process, avoiding the pollution of the soil and subterranean waters. The use of vinasse (stillage) as a buffering agent in the process of enzymatic hydrolysis of lignocellulosic biomasses is comprised in a patent application which applicant is Centro de Tecnologia Canavieira—CTC, duly filed at the INPI [Brazilian Patent and Trademark Office] with filing number PI 1101295-1.

With regard to temperature, one form of realization of the present invention consists in the use, as heat sources, of the flegmass stream (3), of the hydrated alcohol vapor stream (4) originating from the alcohol rectifying column and/or of the vinasse (stillage) stream (5) (see FIG. 6).

The separation of sugars (solution of C6 sugars) generated in the hydrolysis tales place in the "S2" system, wherein various technologies may be applied, as is known by a technician skilled in the art (filtration, centrifugation, compression, etc.). In one form of realization, the separation may occur with the use of a part of the flegmass stream (3), as a source of hot water (FIG. 6). The solid phase resulting from this step can be sent to the boiler or allocated for other commercial purposes, while the hydrolyzed liquor, according to a preferred embodiment of the present invention, is sent directly to the fermentation sector of the 1G plant (in diluted or concentrated form), as illustrated in FIG. 2.

Within the scope of the process that constitutes the object of the present invention, the feeding of the conventional fermentation with the hydrolyzed liquor represents a further point of integration between the 1G and 2G processes. In the specific case of Brazilian sugar and alcohol plants, the hydrolyzed liquor can be used to dilute the molasses, thereby substituting partially or entirely the water used in this operation, until there is reached a concentration between 10° Brix and 50° Brix, more preferentially between 16° Brix and 30° Brix. In autonomous distilleries, the above mentioned hydrolyzed liquor should be evaporated before being sent over to the fermentation step.

Figure 2:
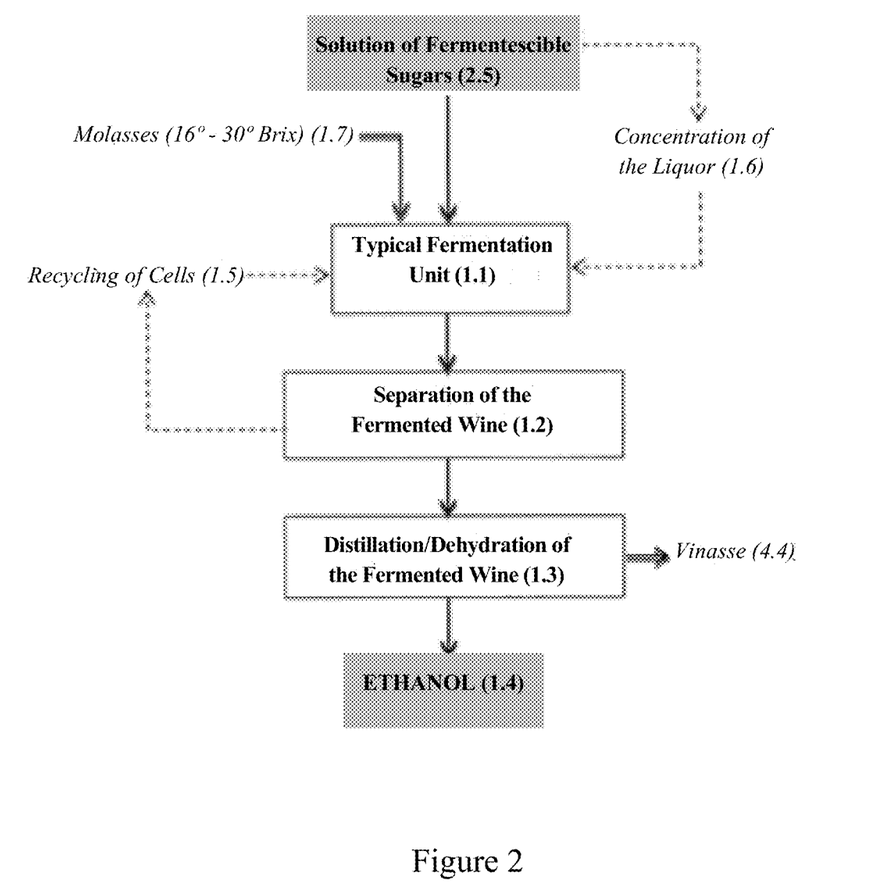
FIG. 2 depicts a schematic drawing of the conventional process for production of ethanol (1G) being fed with fermentescible sugars (C6) produced at the enzymatic hydrolysis step (2G process), followed by the subsequent steps of fermentation (1.1), separation of the fermented wine (1.2), distillation/dehydration of the fermented wine (1.3), ethanol produced (1.4), cell recycling (1.5), concentration of the hydrolyzed juice (1.6), molasses (16°-30° Brix) (1.7) and vinasse (stillage) (4.4).

Therefore, the fermentescible sugars, either those originating from hydrolysis of the biomass or those originating from the sugarcane juice/molasses, are fermented with the use of the infrastructure installed in the industrial units and the same microorganism (FIG. 2). In this fermentation process, it is possible to operate with or without cell recycling and in continuous mode, semi-continuous mode (fed-batch) or discontinuous mode (batch). In one form of realization, the process temperature can be maintained within the optimal range by using a part of the streams stored in the heat recovery system (vapor stream generated in the vessel (RF), stream (7, and/or flegmass stream (3)) illustrated in FIG. 6.

After the fermentation, the must is subjected to a solid-liquid separation process, wherein occurs the separation of the fermented wine from the biomass (leaven) used in the process. Typically this separation process takes place by way of centrifugation, although other methods may equally be used for this purpose; and the recycling of cells can either or not occur. Subsequently, the wine is sent over to the distillation system for obtainment of the end product, generating vinasse (stillage) as a "byproduct".

This step is represented in FIG. 3, wherein the alcohol contained in the wine concentrates until points near the azeotrope point, since the ethanol-water is a non-ideal mixture.

Figure 4:
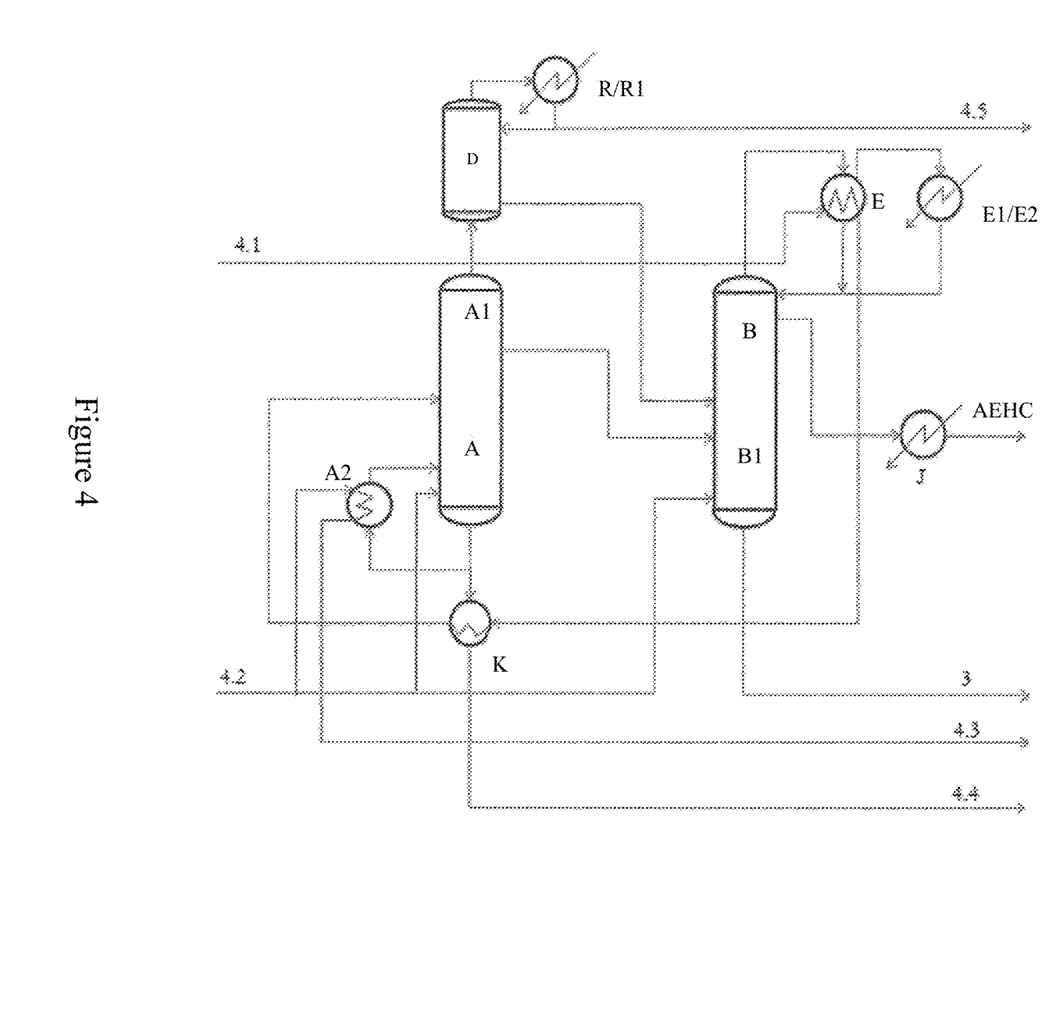
FIG. 4 illustrates the process of distillation of hydrated alcohol, without considering the reuse of energy and effluents, pointing out the essential streams and equipment from the feeding of the wine until the obtainment of the end product (hydrated alcohol). Furthermore, there are also shown the stripping system (A), degassing of wine (A1), concentration of second-generation alcohol (D), rectifying of alcohol (B and B1), heat exchangers (E, E1, E2, R and R1), flegmass stream (3), wine (4.1), steam (4.2), condensate (4.3), vinasse (stillage) (4.4), second-generation alcohol (4.5) and hydrated alcohol fuel (AEHC).
Figure 5:
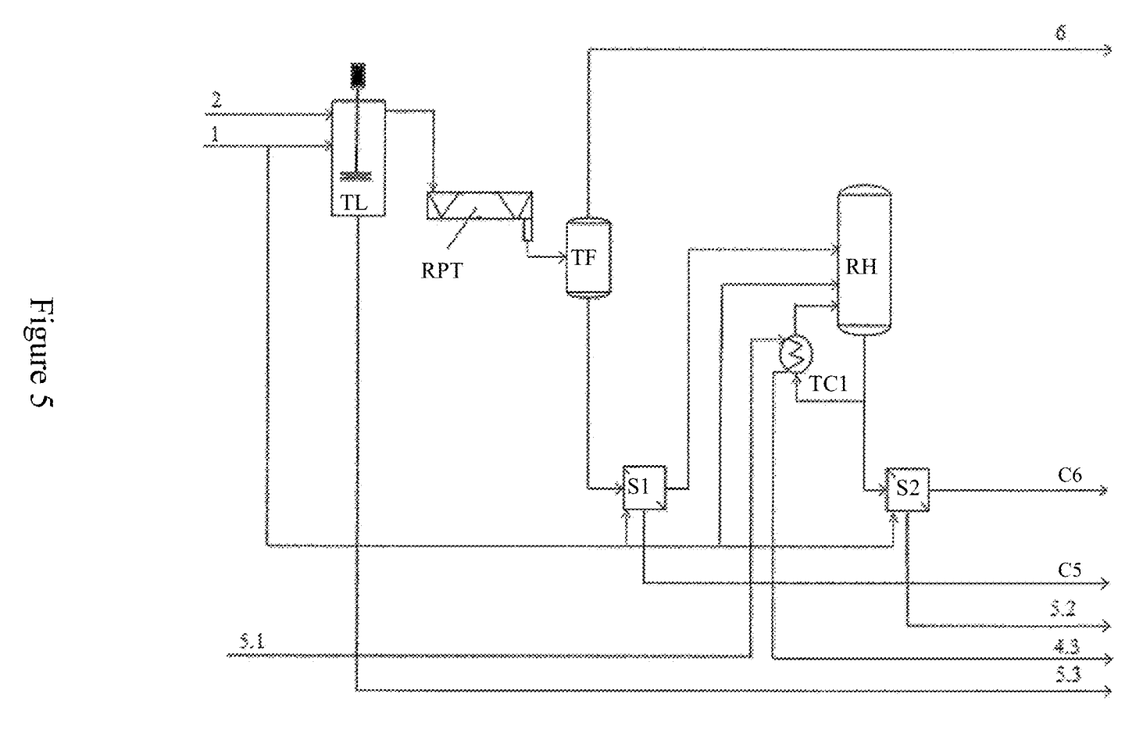
FIG. 5 is a simplified flow diagram of the process of preparation of second generation (2G) ethanol, without considering the reuse of energy and effluents. The flow diagram shows the essential streams and equipment from the feeding of the biomass until the obtainment of the solution of fermentescible sugars (mostly glucose), in addition to the system for separating the sugars (S1 and S2), treated water (1), biomass (2), low pressure steam (5.1), "flash" vapor (6), C5 and C6 streams, cellulignin (5.2), condensate (4.3) and impurities (5.3).

The conventional process that is most frequently found in hydrated ethanol production units consists in the use of 5 columns: A, A1, D, B and B1, as schematically depicted in FIG. 4. Of those columns, the set comprised by columns A, A1 and D is known as the stripping system (A), wine degassing (A1) and second-generation alcohol concentration (D). On the other hand, columns B and B1 are most widely known as alcohol rectifying columns.

The function of column (A) is to withdraw from the wine the substances of higher volatility and the gasses dissolved therein, in addition to completing the heating of the feed stream. The wine is fed at the top of column A1 and the phlegm, with a mass concentration of ethanol of approximately 40%, is withdrawn at the top of column A. The top stream of column A1 is sent to column D, wherein occurs the concentration of the most volatile substances present in the wine. The vapor originating from the top of column D is condensed in exchangers R and R1 and a part thereof returns as reflux, being fed at the top of column D, and another part is withdrawn as second-generation alcohol. From the bottom of column A there is withdrawn a stream named vinasse (stillage), which although it is currently used only as a fertilizer, finds a nobler application within the scope of the instant application. The phlegm, originating from column A, is fed to column B, in vapor phase, where some impurities, such as fusel oil, are removed. In this column, the phlegm is concentrated until reaching a maximum concentration of 92.3% per mass of ethanol. The vapor obtained at the top of column B is partially condensed in the exchanger E, wherein occurs a partial recovery of heat for heating the wine, and subsequently the remaining vapor is condensed in exchangers E1 and E2. The bottom product of column B1 is designated as flegmass and should contain at most 0.02% by mass of ethanol. The vapor required to distillate the wine and rectify the alcohol is supplied at the bottom of columns A and B1. The vapor may be injected directly onto the base of the column by spurting, which is the typical scheme when using juice vapor (0.8 barg) or by indirect exchange, with the application of heat exchangers, for escape vapor (1.5 barg).

In the present invention there is proposed the use of a system for recovering the energy available in the "flash" vapor stream (6), as represented in FIG. 6, to supply a part of, or the total amount, of the energy required in the production of first generation (1G) ethanol. The heat recovery system RF is basically comprised by heat exchangers, separation vessels, control systems and further accessories required for the continuous and stable operation of the said system. The streams 7 and 10 of FIG. 6, generated in the cited RF system, may be used to complement the steam network already existing in the industry, or may be used independently in the existing equipment, by means of heat exchangers or by direct injection. The RF system according to the present invention may operate within a wide range of pressure, between 0.5 and 5 barg, more preferably in the range between 0.8 and 1.5 barg.

The energy supplied at the base of the distillation columns A and B1 is partially reused by means of preheating of the wine originating from the fermentation. This thermal integration recovers for reuse, in average 40% of the energy available in the top stream of rectifying column B. Therefore, about 60% of the energy is transferred to the cooling water and subsequently to the environment, by means of the cooling system (see FIG. 4).

As disclosed in the instant application, part of the stream originating from the top of rectifying column B will be sent to the hydrolysis system (RH), as a heat source for heating internal streams and maintaining the hydrolysis reaction (RH) temperature at optimum level (see FIG. 6).

As illustrated in FIG. 4, the streams of vinasse (stillage) (4.4) and flegmass (3) were not used in conventional processes, but rather sent to be used in sugarcane cultivation for fertirrigation, in the case of Brazil, or evaporated, in countries where there are in place restrictions to the use of the vinasse (stillage) as a fertilizer. In the present invention, the flegmass stream (3), also illustrated in FIG. 6, may be used as a source of hot and clean water for the steps of cleaning of the biomass (TL), extraction of the hemicellulose from the pretreated biomass (S1), extraction of the glucose from the cellulignin cake (S2), to correct the solids content in the hydrolysis system (RH) and/or as replenishment water for the RF system.

Additionally, the present invention may be complemented by document No. [BR] PI 1101295-1, wherein the vinasse (stillage) stream is used as a buffering agent in the reaction of enzymatic hydrolysis of the biomass.

Thus, the present invention provides a reduction in the operating cost of the integrated 1G/2G process and a rational and efficient use of the available natural resources. Its application is immediate and it is not restricted to processes for the production of 1G/2G ethanol that comprise the steps mentioned below herein, although not being limited thereto:

i) Pretreatment of the biomass (either or not clean) by means of vapor, optionally with the use of enzymes and/or chemicals, wherein a part of the said vapor is stored in a heat recovery system;

ii) Separation of the sugars (mostly sugars with five carbon atoms—C5) generated in the pretreatment by methods known in the art, such as compression, centrifugation, washing followed by filtration, washing followed by centrifugation, washing followed by decanting, washing followed by evaporation, among others, using a part of the flegmass stream (3), originating from the rectifying column(s) (B and/or B1) and/or cleaning of the fermenters, illustrated in FIG. 6;

iii) Enzymatic hydrolysis of the pretreated biomass using as a heating source the flegmass stream (3); hydrated alcohol vapor stream (4) originating from the alcohol rectifying column and/or vinasse (stillage) stream (5) (see FIG. 6);

iv) Separation of the solution containing the desired sugars from the residual lignin-rich fiber (cellulignin) using methods known in the art, such as compression, centrifugation, washing followed by filtration, washing followed by centrifugation, washing followed by decanting, washing followed by evaporation, among others, using a part of the flegmass stream (3) originating from the rectifying column(s) (B and/or B1) and/or cleaning of the fermenters, as per FIG. 6;

v) Fermentation of the sugary solution obtained in step "iv" together with the juice and/or molasses, using a part of the streams stored in the heat recovery system (vapor stream generated in the vessel (RF), stream (7), and/or flegmass stream (3)), illustrated in FIG. 6;

vi) Separation of the fermented wine by centrifugation and/or other solid-liquid separation methods using a part of the streams stored in the heat recovery system (vapor stream generated in the vessel (RF), stream (7), and/or flegmass stream (3)), illustrated in FIG. 6;

vii) Distillation/Dehydration of the ethanol produced in the fermentation using a part of the stream stored in the heat recovery system, preferably the vapor stream generated in the vessel (RF), stream (7) (see FIG. 6).

Optionally, prior to the above described step i), there may be performed the cleaning of the biomass by using a part of the flegmass stream (3), originating from the rectifying column(s) (B and/or B1) and/or cleaning of the fermenters.

The above mentioned heat recovery system may receive, store and supply a part or the totality of the energy required in the production of first generation (1G) ethanol. The heat recovery and reuse system (RF) of FIG. 6 may be comprised by heat exchangers, separation vessels, control systems and further accessories required for the continuous and stable operation thereof. It can be operated within a wide range of pressures, between 0.5 and 5 barg, more preferably within the range from 0.8 to 1.5 barg.

In a form of realization, the distillation is the separation process that is commonly used in the ethanol producing plants for distilling the de-leavened wine for the production of alcohol (hydrated and anhydrous) and the most frequent configuration of that process in the hydrated and/or anhydrous ethanol producing units is illustrated in FIG. 4, by items A, A1, D, B and B1.

System for Integrated Production of Alcohol of First and Second Generations

The integration between the 1G and 2G processes according to the present invention occurs by means of the utilization of streams and/or effluents produced in the 1G ethanol production process for supplying partially or entirely the energy and effluents demand of the 2G ethanol production plant, and vice-versa, aiming to maximize the production of biofuel from the same quantity of biomass that is supplied to the industry.

Therefore, one other object of the present invention consists in the provision of a system for integrated production of 1G and 2G ethanol that allows the reuse of streams and/or effluents present in the 1G ethanol production process to supply a part of the energy requirements of the 2G ethanol production plant and vice-versa, in order to provide a rational and efficient use of the available natural resources towards maximizing the global production of biofuel from the same quantity of biomass that is supplied to the industry. Such system comprises the following points of integration, as illustrated in FIG. 6:

i) Use of the flegmass stream (3), originating from the rectifying column(s) (B and/or B1) as a source of hot water to generate vapor in the vessel (RF);

ii) Use of the flegmass stream (3), originating from the rectifying column(s) (B and/or B1) as a source of hot water for the separation and recovery system in (S1) and (S2);

iii) Use of the flegmass stream (3), originating from the rectifying column(s) (B and/or B1) as a source of hot water for controlling the solids content in the enzymatic hydrolysis step;

iv) Use of the flegmass stream (3), originating from the rectifying column(s) (B and/or B1) as a source of hot water for directly or indirectly heating the enzymatic hydrolysis reactor(s) (RH);

v) Use of the flegmass stream (3), originating from the rectifying column(s) (B and/or B1) as a source of hot water for cleaning the biomass that is fed to the process;

vi) Use of the alcoholic stream (4) from the top of the rectifying column(s) (B and/or B1) in vapor phase, as a source of heating for the biomass hydrolysis reactor(s);

vii) Use of the vinasse (stillage) stream (5) as a source of direct or indirect heating for the biomass hydrolysis reactor(s) (RH);

viii) Use of the vinasse (stillage) stream (5) as a source of buffering solution for controlling the pH of the enzymatic hydrolysis reaction;

ix) Use of the energy contained in the "flash" vapor stream (6), generated after the pretreatment of the biomass, for generating steam in the vessel (RF);

x) Use of the vapor generated in the steam vessel (RF), stream (7), to provide energy for operating the stripping column(s) A and degassing column(s) A1 and for operating the rectifying column(s) (B and/or B1) or equivalent(s) thereof;

xi) Use of the vapor generated in the steam vessel (RF), stream (7), as a source of direct or indirect heating for the biomass hydrolysis reactor(s);

xii) Use of the vapor generated in the steam vessel (RF), stream (7), as a source of direct heating, e.g., spurting (stream 8), for the bottom of columns A, A1, B and B1;

xiii) Use of the return flow of all or a part of the condensate from the vapor of stream (7) when the energy is recovered by indirect exchange, for the steam vessel RF;

xiv) Use of the treated water, stream (9), for generating vapor in the RF vessel; and xv) Use of the vapor generated in the vessel (RF), stream (10), to provide energy for preheating the feed streams to the reactor (RPT) or equivalent(s) thereof.

The interlinking points described above may all be used to realize the process of integrated production of 1G and 2G ethanol, as well as it is possible, as may be easily noted by a technician skilled in the art, and depending on the plant configuration of the ethanol producing plant itself, to use a combination of the integration points listed above.

Therefore, the system according to the present invention additionally comprises the following items (see FIG. 6):

i) at least one means for connecting the outlet of the vessel (TF) to the inlet of the steam vessel (RF);

ii) at least one means for connecting the outlet(s) of the rectifying column(s) (B and/or B1) to the steam vessel (RF);

iii) at least one means for connecting the outlet(s) of the rectifying column(s) (B and/or B1) to the separation and recovery systems in (S1) and (S2);

iv) at least one means for connecting the outlet(s) of the rectifying column(s) (B and/or B1) to the hydrolysis reactors (RH) and/or the biomass cleaning system (TL);

v) at least one means for utilizing treated water available in the plant to generate steam in the vessel (RF);

vi) at least one means for connecting the outlet(s) of the steam vessel (RF) to the stripping column(s) A and degassing column(s) A1 and to the rectifying column(s) (B and/or B1) or equivalent(s) thereof;

vii) at least one means for connecting the outlet(s) of the steam vessel (RF) to the reactor(s) (RPT) or equivalent(s) thereof;

viii) at least one means for connecting the outlet(s) of the steam vessel (RF) to the hydrolysis reactor(s);

ix) at least one means for returning the condensate of the vapor of stream (7), when the energy is recovered by indirect exchange, to the steam vessel RF; and x) at least one means for employing the alcoholic stream (4) from the rectifying column(s) (B and/or B1) in vapor phase as a heat source for heating the biomass hydrolysis reactor(s);

and combinations of part of the elements described above.

The said "means" comprehend, but are not limited to equipment such as shell and tube and/or plate-type heat exchangers, in their various configurations, such as, for example, thermosyphon, "falling film" and other types, for recovering, bi indirect exchange, the energy contained in the "flash" vapor stream (6), generated after the pretreatment of the biomass and in the alcoholic stream (4) from the top of the rectifying column(s) (B and/or B1) in vapor phase. Furthermore, there is used instrumentation and control in the vessel (RF) for generating steam, such instruments being preferably represented by pressure controllers, level controllers, flow and/or temperature controllers.

The elements described above herein may be combined wholly or in part, as may be easily noted by a technician skilled in the art, depending on what is most adequate for the structure itself of the ethanol production plant.

In FIG. 6 there is illustrated the system proposed in the instant application, representing the streams and points of integration of the integrated 1G/2G process described above.

The present invention is further described by the merely illustrative and non-limitative examples described in the following.

Example 1

The energy contained in the "flash" vapor stream (6) was reused to generate steam in the vessel (RF), by means of the use of one or multiple exchangers to recover, by indirect exchange, the energy contained in the "flash" vapor stream (6), generated after the pretreatment of the biomass by steam explosion or other techniques. The exchangers used were of the shell and tube and/or plate types, in their various configurations such as thermosyphon, "falling film" and others, for recovering, by indirect exchange, the energy contained in the "flash" vapor stream (6). In equivalent embodiments, there may be used one or more steam vessels (RF) for generating steam from the energy recovered from the "flash" vapor stream (6).

According to the concept of reuse of effluents, the flegmass stream (3) originating from the rectifying column(s) B and/or B1 or equivalent(s) thereof after the use in cleaning the fermenters, can be employed as a source of water for generating steam in the steam vessel (RF).

Additionally, there may be used treated water for the boiler or any type of condensate of heating vapor, designated as stream 9 in the flow diagram, as a source of water for generating steam in the steam vessel (RF).

In the scheme described herein there was used an instrumentation and control system for the process variables of the steam vessel (RF), such as: pressure, level, flow and temperature.

The stream(s) generated in the vessel (RF) provide in part or totally the energy required in the various steps of the instant arrangement are herein designated as, for example, stream (7), for supplying energy to the first generation ethanol producing unit or the stream designated as stream (10), which is employed for heating the streams of the pretreatment system (RPT), illustrated in FIG. 6.

In the specific example, the stream (7) is employed as a heat source, wholly or in part, for the second generation ethanol production unit and supplies a part or the whole energy required for operating the stripping column(s) (A) and degassing column(s) (A1).

The schematic drawing of FIG. 6 provides the use of shell and tube type exchangers, in their various configurations such as thermosyphon and "falling film" and other types for recovering, by indirect exchange, the energy contained in the "flash" vapor stream 7, providing a part or the totality of the energy required for the operation of the stripping column(s) A and degassing column(s) A1 or equivalent(s) thereof. In the present configuration, plate type exchangers were also used for recovering, by means of indirect exchange, the energy contained in the "flash" vapor stream 7, providing a part or the totality of the energy required for the operation of the stripping column(s) A and degassing column(s) A1.

The present example also provides the use of direct spurting of the vapor of stream (7) to provide a part or the totality of the energy required for operating the stripping column(s) A and degassing column(s) A1.

In the present example, the stream (7) generated in the vessel (RF) is employed for providing a part or the totality of the energy required to operate the rectifying column(s) B and/or B1 or equivalent(s) thereof.

In the example disclosed herein, there were used exchangers of the shall and tube type, in their various configurations such as thermosyphon and "falling film" and other types for recovering, by indirect exchange, the energy contained in the "flash" vapor stream 7, providing a part or the totality of the energy required for the operation of the rectifying column(s) B and/or B1 or equivalent(s) thereof.

The recovery of energy, as described above, can also be realized by means of plate type exchangers, in their various configurations, for recovering, by indirect exchange, the energy contained in the "flash" vapor stream (7), providing a part or the totality of the energy required for operating the rectifying column(s) B and/or B1 or equivalent(s) thereof.

The schematic drawing of FIG. 6 also provides the direct spurting of the vapor of stream (7) for provision of a part or the totality of the energy required for the operation of the rectifying column(s) (B and/or B1).

In the process configuration described herein, a part or all the condensate from the vapor of stream (7) returns to the steam vessel (RF), when the energy is recovered by indirect exchange.

According to the model of FIG. 6, the flegmass stream (3) originating from the rectifying column(s) (B and/or B1) or after the use in cleaning the fermenters, is employed as a source of hot water for the biomass cleaning system (TL), irrespective of the technique, the equipment and the configurations adopted in the cleaning system.

The scheme also provides the use of exchangers of the shell and tube type, plate type or any indirect heat exchange system, listed as (TC1) in FIG. 6, for controlling the temperature in the flegmass stream (3) at the inlet of the biomass cleaning system (TL).

In the proposed example, the flegmass stream (3), originating from the rectifying column(s) (B and B1) or equivalent(s) thereof, after the use in cleaning the fermenters, is employed as a source of hot water for the separation and recovery system of the stream (C5) of pretreated biomass, listed as (S1) in FIG. 6, irrespective of the technique, the equipment and the configurations adopted in this separation and recovery system.

In order to warrant a correct performance of the system (S1), there were used shall and tube type exchangers, plate-type exchangers or any other indirect heat exchange system, listed as (TC5) in FIG. 6), to modulate the temperature of the flegmass stream (3) on entry thereof into the system (S1).

According to the configuration proposed in FIG. 6, the flegmass stream (3), originating from the rectifying column(s) B and/or B1 or equivalent(s) thereof, after the use in cleaning the fermenters, is employed as a source of hot water for the separation and recovery system of the stream of (C6) of the cellulignin cake, listed as (S2) in FIG. 6.

The present example provides the use of exchangers of the shall and tube type, plate type or any indirect heat exchange system, listed as (TC6) in FIG. 6, for modulating the temperature of the flegmass stream (3) on entry thereof into the system (S2).

The flegmass stream (3), originating from the rectifying column(s) (B and/or B1) or equivalent(s) thereof after use in cleaning the fermenters, was employed as a source of hot water for the hydrolysis reactors, listed as (RH) in FIG. 6, irrespective of the technique, the equipment and the configurations adopted in this biomass hydrolysis system.

According to the configuration of the present invention, exchangers of the shell and tube type, of plate type or any system for indirect heat exchange, listed as (TC8) in FIG. 6, were used to modulate the temperature of the flegmass stream (3) on entry thereof into the system (RH).

The scheme described in FIG. 6 employs the alcoholic stream (4) from the top of the rectifying column(s) (B and/or B1) or an equivalent thereof, in vapor phase, as a heating source in the biomass hydrolysis step.

At this point of thermal recovery there were used exchangers of the shell and tube type, of plate type or any system for indirect heat exchange, listed as (TC3) in FIG. 6, to recover the energy contained in the stream (4), supplying the energy required to heat the hydrolysis system (RH) until reaching the optimum process temperature, irrespective of the technique, the equipment and the configurations adopted in this system for hydrolysis of the biomass.

In the system presented in FIG. 6 there were used instrumentation and control systems to read and control the process variables in the rectifying column(s) (B and/or B1), such as: pressure control, flow rate control and temperature control, towards stabilizing and controlling the energy recovery system proposed in the present invention.

Example 2

This example illustrates a possible embodiment of the system, representing a practical application of the present invention.

The cleaning system (TL) is fed with 50 tons/day of biomass, the latter comprising about 2 to 15% by weight of impurities. This stream may consist in a composition, in any proportion, of bagasse and straw. Concurrently with the feeding of the biomass, about 5 m$^3$ [cubic meters] per hour of flegmass (3) are fed, in continuous mode, to the system (TL). The flegmass will be used within the temperature range of 30 to 105° C., more preferably in the range of from 85° C. to 100° C.

Subsequently in the process, the biomass upon been cleaned and homogenized is preheated to a temperature in the range of from 80 to 150° C., using the stream (10) that originates from the steam recovery system (RF). After the pretreatment system (RPT), the biomass is rapidly decompressed in the "flash" system (TF), with the pressure varying in the range of from 26 barg to atmospheric pressure. In this step, the vapor stream (6) with a pressure that may vary within the range of 0.5 to 5 barg, is generated and fed to the steam recovery system (RF). The operation of the system (RF) may take place within a pressure range that varies between 0.5 and 6.0 barg, preferably at a pressure of 1.5 barg. In this example, about 1.0 ton per hour of steam is generated in the system (RF), which corresponds to 40% of the steam used in the reactor (RPT). A part of this generated steam, about 80%, will be utilized in the alcohol distillation step, by means of the stream (7), which is within the pressure range of 0.5 to 3.0 barg. A fraction of the flegmass stream (3), approximately 1.5 m$^3$ [cubic meters] per hour, is used to maintain the operating volume of the system (RF) within the temperature range of 50 to 105° C.

After the pretreatment, the biomass is fed to the separation system (S1) wherein the solubilized fraction of the hemicellulose is separated from the cellulose fiber. In this step, about 10 m$^3$ [cubic meters] per hour of flegmass originating from the distillation is fed, at a temperature within the range of 50 to 105° C., to the separation system (S1).

In the following step, approximately 2.0 tons per hour of biomass having been pretreated and separated from the hemicellulose fraction is fed to the hydrolysis reactor (RH). In order to warrant the operation of the reactor(s) at the optimum temperature of the enzymatic reaction, which may vary within the range of from 35 to 70° C., there are used approximately 5.0 tons per hour of the stream (4), which constitutes a part of the alcoholic vapor originating from the top of the rectifying column "B". The content of solids in suspension in the reactor (RH) is kept within the range of 8 to 40%, by way of the addition of flegmass (3) and vinasse (stillage) (5). Upon completion of the hydrolysis reaction, the reaction medium is fed to the separation system (S2), wherein the glucose fraction is separated from the lignin fraction and from the unreacted cellulose fraction. The glucose, present in the cellulignin cake generated in this step, will be displaced with approximately 50 m$^3$ [cubic meters] per hour of flegmass originated from the stream (3). The glucose stream, designates as C6 in FIG. 6, is sent over to fermentation.

As may be understood from that which is disclosed herein, the use of the present invention is economically interesting, since it allows the optimization of already existing first and second generation ethanol producing facilities or it may be applied in new projects to reduce the operating cost of the unit. Furthermore, it should be understood that the present invention encompasses other modalities and embodiments beyond those described in the instant patent application.

The invention claimed is:

1. A system for integrated production of ethanol of first and second generations, comprising:

a heat recovery vessel;

one or more enzymatic hydrolysis reactors including one or more biomass hydrolysis reactors in communication with the heat recovery vessel;

a stripping system including a scrubbing column and a drainage column in communication with the one or more enzymatic hydrolysis reactors; and an alcohol rectifying system including at least one rectifying column in communication with the stripping system;

the heat recovery vessel being in communication with the alcoholic rectifying system, the heat recovery vessel configured to receive a flegmass stream from the at least one rectifying column, the heat recovery vessel configured to generate steam from the flegmass stream;

separation and recovery systems in communication with the alcohol rectifying system, the separation and recovery systems configured to receive the flegmass stream from the at least one rectifying column;

the one or more enzymatic hydrolysis reactors being in communication with the alcohol rectifying system, the one or more enzymatic hydrolysis reactors configured to receive the flegmass stream, and control solids content and heat the one or more enzymatic hydrolysis reactors with the heat from the received flegmass stream, the one or more enzymatic hydrolysis reactors configured to receive an alcoholic stream in a vapor phase and heat the one or more biomass hydrolysis reactors with the heat from the received alcoholic stream in the vapor phase;

a biomass cleaning system in communication with the alcohol rectifying system, the biomass cleaning system configured to receive the flegmass stream as an input to clean a biomass;

the stripping system in communication with the one or more enzymatic hydrolysis reactors, the one or more enzymatic hydrolysis reactors configured to receive a vinasse stream, and heat the one or more biomass hydrolysis reactors with heat from the vinasse stream, the one or more enzymatic hydrolysis reactors further configured to control a pH level of an enzymatic hydrolysis reaction using the vinasse stream;

a flash tank vessel in communication with the heat recovery vessel, the heat recovery vessel configured to receive vapor from the flash tank vessel and generate vapor, at least in part, from energy contained in the received vapor from the flash tank;

the stripping system in communication with the heat recovery vessel, the stripping system configured to receive the vapor generated in the heat recovery vessel and operate the scrubbing column and the drainage column using energy contained in the received vapor generated in the heat recovery vessel, the stripping system further configured to repeatedly inject and withdraw from a bottom of the scrubbing column and the drainage column, the received vapor generated in the heat recovery vessel;

the alcohol rectifying system in communication with the heat recovery vessel, the alcoholic rectifying system configured to receive the vapor generated in the heat recovery vessel and operate the at least one rectifying column using energy contained in the received vapor generated in the heat recovery vessel, the alcohol rectifying system further configured to repeatedly inject and withdraw from a bottom of the at least one rectifying column, the received vapor generated in the heat recovery vessel;

the one or more enzymatic hydrolysis reactors in communication with the heat recovery vessel, the one or more enzymatic hydrolysis reactors configured to receive the vapor generated in the heat recovery vessel and heat the one or more biomass hydrolysis reactors with the heat from the received vapor generated in the heat recovery vessel;

the heat recovery vessel configured to receive at least a part of condensate of the vapor generated in the heat recovery vessel;

a source of treated water in communication with the heat recovery vessel, the heat recovery vessel configured to receive the treated water and generate vapor at least in part from the treated water;

a pretreatment reactor in communication with the heat recovery vessel, the pretreatment reactor configured to receive the vapor generated in the heat recovery vessel and preheat feed streams using energy contained in the received vapor generated in the heat recovery vessel.

2. A system, as claimed in claim 1, further comprising:

at least one shell for connecting an outlet of a flash tank vessel to an inlet of the heat recovery vessel;

at least one shell to connect outlet(s) of the at least one rectifying column to the heat recovery vessel;

at least one shell to connect the outlet(s) of the at least one rectifying column to the separation and recovery systems;

at least one shell to connect the outlet(s) of the at least one rectifying column to the one or more biomass hydrolysis reactors and/or to the biomass cleaning system;

at least one shell to recover treated water available in a plant to generate vapor in the heat recovery vessel;

at least one shell to connect outlet(s) of a vapor vessel to the drainage column and the scrubbing column and to the at least one rectifying column;

at least one shell to connect the outlet(s) of the vapor vessel to the pretreatment reactor;

at least one shell to connect the outlet(s) of the vapor vessel to the one or more biomass hydrolysis reactors;

at least one shell to return the condensate of the vapor of stream, when the energy is recovered by indirect exchange, to the heat recovery vessel; and at least one heat exchanger for employing alcoholic stream of the at least one rectifying column in the vapor phase as a heat source for heating the one or more biomass hydrolysis reactors.

3. A system, as claimed in claim 2, wherein the at least one heat exchange is a tube type heat exchanger or a plate type heat exchanger.

4. A system, as claimed in claim 2, wherein the heat recovery vessel includes instruments and controls.

5. A system, as claimed in claim 4, wherein the instruments are selected from the group consisting of pressure controllers, level controllers, flow controllers and temperature controllers.

6. A process for integrated production of ethanol of first and second generations employing the system of claim 1, comprising:

pre-treating a biomass;

conducting enzymatic hydrolysis of the pretreated biomass;

separating a solution containing the fermentescible sugars from lignin-rich residual fiber (cellulignin);

fermenting the solution obtained in the separating step together with sugars of a sugarcane broth and/or molasses;

separating fermented wine; and distilling/dehydrating ethanol produced in the separating step.

7. A process, as claimed in claim 6, wherein the pretreating step includes use of vapor, where part of the energy employed in this operation is recovered by a heat recovery system;

wherein the separating of the sugars step includes use of a part of the flegmass stream, originating from the rectifying column(s) and/or from cleaning of fermenters;

wherein the conducting step includes utilizing as a heat source the flegmass stream, the hydrated alcohol vapor stream, originating from a alcohol-rectifying column, and/or from the vinasse stream;

wherein the separating of the sugars step includes utilizing part of the flegmass stream, originating from the rectifying column(s), and/or from the cleaning of the fermenters;

wherein the fermenting step includes utilizing part of the streams stored in the heat recovery system for cleaning, sterilization, cooling or a combination of these operations;

wherein the separating step of the fermented wine includes utilizing a part of the stream stored in the heat recovery system, vapor stream generated in vapor vessel, stream, and/or the flegmass stream for cleaning, sterilization, cooling or a combination of these operations;

wherein the distillation/dehydrating step includes using part of the stream stored in the heat recovery system.

8. A process, as claimed in claim 7, further comprising cleaning the biomass prior to the pretreatment step.

9. A process, as claimed in claim 8, wherein the cleaning is conducted with the use of part of the flegmass stream originating from the rectifying column(s) and/or from the cleaning of the fermenters.

10. A process, as claimed in claim 6, wherein, in the separating of the fermented wine step, molasses is diluted with hydrolyzed broth until there is reached a concentration between 10° Brix and 50° Brix.

11. A process, as claimed in claim 7, wherein the heat recovery system includes heat exchangers, separation vessels, control systems and other accessories required for the continuous and stable operation thereof.

12. A process, as claimed in claim 7, wherein the pretreating step includes the use of chemical or biological catalysts.

* * * * *